United States Patent [19]

Meybeck

[11] Patent Number: 5,279,834
[45] Date of Patent: * Jan. 18, 1994

[54] PHARMACEUTICAL OR COSMETIC COMPOSITION CONTAINING HYDROQUINONE AND KOJIC ACID

[75] Inventor: Alain Meybeck, Courbevoie, France

[73] Assignee: LVMH Recherche, Colombes, France

[*] Notice: The portion of the term of this patent subsequent to Nov. 17, 2009 has been disclaimed.

[21] Appl. No.: 917,516

[22] Filed: Jul. 17, 1992

Related U.S. Application Data

[63] Continuation of Ser. No. 744,650, Aug. 8, 1991, abandoned, which is a continuation of Ser. No. 458,737, Dec. 11, 1989, abandoned.

[30] Foreign Application Priority Data

Jun. 12, 1987 [FR] France .................. 87 08236

[51] Int. Cl.$^5$ .................. A61K 9/127; A61K 7/02
[52] U.S. Cl. ..................... 424/450; 424/62; 424/420; 424/401
[58] Field of Search ............. 424/450, 62, 420, 401

[56] References Cited

U.S. PATENT DOCUMENTS

| | | | |
|---|---|---|---|
| 3,856,934 | 12/1974 | Kligman | 424/62 |
| 4,241,046 | 12/1980 | Papahadjopoulos | 424/450 |
| 4,696,813 | 9/1987 | Higa | 424/59 |
| 4,797,285 | 1/1989 | Barenholz et al. | 424/450 |
| 4,847,267 | 7/1989 | Deckner et al. | 514/311 |
| 4,990,330 | 2/1991 | Oyama | 424/59 |

FOREIGN PATENT DOCUMENTS

| | | |
|---|---|---|
| 2383663 | 11/1978 | France . |
| 8504101 | 9/1985 | PCT Int'l Appl. . |
| 1303566 | 1/1973 | United Kingdom . |
| 1319455 | 11/1973 | United Kingdom . |
| 2052973 | 2/1981 | United Kingdom . |

OTHER PUBLICATIONS

Kenkyusho Chem Absts 102, 1985 #12207k.

*Primary Examiner*—Thurman K. Page
*Assistant Examiner*—G. Kishore
*Attorney, Agent, or Firm*—Bryan Cave

[57] ABSTRACT

The invention relates to a cosmetic or pharmaceutical composition, containing hydroquinone and kojic acid or a derivative thereof, especially the salts or esters thereof. The hydroquinone and/or kojic acid component is in a form which is at least partially incorporated into liposomes.

The combination of these components in liposomes makes it possible to obtain a synergistic effect in their use as topical formulations, especially dermatological or cosmetic compositions, especially for their skin-lightening activity.

9 Claims, No Drawings

PHARMACEUTICAL OR COSMETIC COMPOSITION CONTAINING HYDROQUINONE AND KOJIC ACID

This is a continuation of U.S. application Ser. No. 07/744,650, filed Aug. 8, 1991 now abandoned, which is a continuation of U.S. application Ser. No. 07/458,737, filed Dec. 11, 1989, now abandoned, which is incorporated by reference herein.

The present invention relates essentially to a composition of active principles for the preparation of a pharmaceutical or cosmetic composition, containing hydroquinone and kojic acid in liposomes, and to a pharmaceutical composition, especially a dermatological composition, with skin-lightening or antiinflammatory activity, or a cosmetic composition comprising kojic acid and hydroquinone in liposomes.

A composition with a substantial skin-lightening activity which may be mentioned is the Kligman trio, which is based on a combination of vitamin A acid or tretinoin, hydroquinone and a steroid consisting of dexamethasone. However, the use of such a composition has been limited in practice because of a considerable irritant character caused by the presence of vitamin A acid, which is well known for its irritant character, and undesirable effects due to hypervitaminosis A (see "The Journal of Investigative Dermatology", volume 73, no. 5, part I, pages 354-358, and in particular the penultimate paragraph on page 357, published in 1979).

Furthermore, the use of hydrated lipidic lamellar phases or of liposomes is already known in pharmaceutical compositions or cosmetic compositions in which a variety of active principles are incorporated (French patent document A-2 540 381).

It has now been discovered, totally surprisingly and unexpectedly, that a combination of kojic acid or derivatives thereof, especially salts or esters thereof, and hydroquinone, at least one of which is incorporated into hydrated lipidic lamellar phases or into liposomes, makes it possible to prepare a pharmaceutical composition, especially a dermatological composition, with skin-lightening or antiinflammatory activity, or a cosmetic composition which is particularly advantageous. This activity is without doubt due to a synergistic effect.

Such a synergistic effect is also obtained, in a particularly improved manner, if at least part of a combination of kojic acid or derivatives thereof, especially salts or esters thereof, and hydroquinone is incorporated into hydrated lipidic lamellar phases or into liposomes.

Thus the object of the present invention is to solve the novel technical problem which consists in providing a novel formulation, containing hydroquinone, making it possible to prepare pharmaceutical compositions, especially dermatological compositions, with skin-lightening or antiinflammatory activity, or cosmetic compositions of enhanced efficacy.

The present invention provides the first satisfactory solution to this novel technical problem in a particularly simple manner which is very easy to carry out on the industrial scale.

Thus, according to a first aspect, the present invention provides a composition of active principles for the preparation of a pharmaceutical or cosmetic composition, containing hydroquinone, which also contains kojic acid or derivatives thereof, especially salts or esters thereof, at least one of the substances hydroquinone and kojic acid or derivatives thereof, especially salts or esters thereof, being in a form which is at least partially incorporated into hydrated lipidic lamellar phases or into liposomes.

According to a second aspect, the present invention further relates to a pharmaceutical composition, especially a dermatological composition, with skin-lightening or antiinflammatory activity, or a cosmetic composition, which comprises kojic acid or derivatives thereof, especially salts or esters thereof, and hydroquinone, at least one of the substances hydroquinone and kojic acid or derivatives thereof, especially salts or esters thereof, being in a form which is at least partially incorporated into hydrated lipidic lamellar phases or into liposomes.

Preferably, at least part of the hydroquinone and the kojic acid or derivatives thereof, especially salts or esters thereof, is incorporated into hydrated lipidic lamellar phases or into liposomes.

Preferably, the kojic acid or derivatives thereof, especially salts or esters thereof, represents from 0.5 to 4%, more preferably from 0.5 to 2% and most preferably about 1% by weight, relative to the total weight of the composition.

According to another characteristic of the invention, the hydroquinone preferably represents 0.5 to 6%, more preferably 0.5 to 4% and most preferably about 2% by weight, relative to the total weight of the composition.

The invention further relates to processes for the preparation of the above-mentioned compositions, wherein hydroquinone mixed with kojic acid or derivatives thereof, especially salts or esters thereof, is incorporated as the active principle and at least one of the substances hydroquinone and kojic acid or derivatives thereof, especially salts or esters thereof, is at least partially incorporated into hydrated lipidic lamellar phases or into liposomes.

In the present description and the claims, the term "lipidic" in the expression "lipidic lamellar phase" covers all substances comprising a so-called fatty carbon chain, generally of more than 5 carbon atoms.

According to the invention, amphiphilic lipids are used, i.e. lipids consisting of molecules possessing a hydrophilic group, which can equally well be ionic or non-ionic, and a lipophilic group, these amphiphilic lipids being capable of forming lipidic lamellar phases in the presence of an aqueous phase. The following may be mentioned in particular among these lipids: phospholipids, phosphoaminolipids, glycolipids, polyethoxylated fatty alcohols and optionally polyethoxylated polyol esters. Such substances consist for example of an egg or soya lecithin, a phosphatidylserine, a sphingomyelin, a cerebroside or an ethoxylated polyglycerol stearate.

Further objects, characteristics and advantages will become clear on reading the following explanatory description given with reference to several illustrative Examples, which cannot therefore in any way limit the scope of the invention. In the Examples, the percentages are given by weight, unless indicated otherwise.

EXAMPLE 1 ACCORDING TO THE INVENTION

Preparation of a Composition of Active Principles Containing Hydroquinone and Kojic Acid in Liposomes (Called Composition I1)

1 g of kojic acid and 2 g of hydroquinone are taken and dissolved in 30 ml of methylene chloride to which 2 g of hydrogenated soya lecithin are added, if appropriate in the presence of a lipophilic antioxidant, for example 0.06 g of alpha-tocopherol.

The solution obtained can be treated to give a suspension of liposomes by the well-known process of evaporation in a rotating vessel, which consists in depositing a lipidic layer in the round-bottomed flask of the rotary evaporator by evaporation of the solvent, and then adding water or an appropriate aqueous solution.

It is also possible to use the so-called reversed phase technique described in U.S. Pat. No. 4,224,179.

However, it is preferred to atomize the resulting solution at 65° C. in the manner described in U.S. Pat. No. 4,508,703, producing a fine powder which is dispersed in 200 ml of an aqueous solution buffered to about pH 7.5. In general, the solution used is a solution containing 0.8% of NaCl and 1.5% of $NaH_2PO_4$—called "phosphate buffer"—to which an antioxidizing stabilizer, such as ascorbic acid at a concentration of 0.05%, has been added.

This gives the said suspension of liposomes after homogenization either by means of ultrasound or in a homogenizer under pressure, for example by the process described in U.S. Pat. No. 4,621,023, in which suspension the concentrations of kojic acid, hydroquinone and lecithin are 1%, 2% and 1% respectively.

If, for example, homogenization is effected by treatment with ultrasound for 10 min, a mean liposome size of the order of 112 nm is obtained.

It will be seen that various dilutions can of course be prepared by modifying the amount of kojic acid or hydroquinone added at the start or by increasing the volume of the solution of dispersion, which represents an easy process for the preparation of various concentrations of active substance(s).

This suspension is then converted to a gel, for example by the addition of 1% of a gelling agent such as a vinylic polymer, in particular that marketed under the tradename Carbopol ® 940.

COMPARATIVE EXAMPLE 2

Preparation of a Composition of Active Principles Containing Hydroquinone and Kojic Acid (Called Composition A1)

1 g of kojic acid is dissolved in 14 g of distilled water by heating at 40° C. for 10 minutes, with stirring.

In a separate operation, 2 g of hydroquinone are dissolved in a solution containing 0.5 g of ascorbic acid and 0.4 g of sodium sulfite in 29 g of 95% ethanol.

The aqueous solution of kojic acid and the alcoholic solution of hydroquinone are mixed.

53.1 g of carboxyvinylic polymer gel (Carbopol ® 940) are added to this mixture.

To prepare this gel in the conventional manner, 5 g of Carbopol ® 940 are dispersed in 100 g of water in the presence of preservatives and a chelating agent, and then, after swelling, the dispersion is neutralized to pH 7.5 with triethanolamine.

This gives a gelled composition (A1) containing 2% by weight of hydroquinone and 1% by weight of kojic acid.

COMPARATIVE EXAMPLE 3 (COMPOSITION CALLED A2)

Composition of Liposomes Containing Kojic Acid

The procedure of Example 1 is followed except that only 1 g of kojic acid is added, without hydroquinone.

COMPARATIVE EXAMPLE 4 (COMPOSITION CALLED A3)

Composition of Liposomes Containing Hydroquinone

The procedure of Example 1 is followed except that 2 g of hydroquinone are added, without kojic acid.

COMPARATIVE EXAMPLE 5 (COMPOSITION CALLED A4)

Composition Containing Hydroquinone

A comparative composition in the form of a gel is prepared with the same gel as in Comparative Example 2, only 2% by weight of hydroquinone being incorporated therein.

EXAMPLE 6 ACCORDING TO THE INVENTION

Preparation of a Liposomal Composition Containing Hydroquinone and Kojic Acid in the Aqueous Phase A buffered aqueous solution having the following composition is prepared:

| | |
|---|---|
| kojic acid | 1 g |
| hydroquinone | 2 g |
| ascorbic acid | 0.5 g |
| sodium sulfite | 0.4 g |
| phosphate buffer of pH 7.5 (Example 2) | 44.1 g |

The constituents are stirred at ordinary temperature until solubilization is complete.

2 g of powdered atomized hydrogenated lecithin are then dispersed in the said solution by the method mentioned in Example 1.

The dispersion is stirred for 15 minutes at room temperature to give a suspension of liposomes in which part of the hydroquinone and kojic acid is encapsulated.

This suspension is homogenized by means of ultrasound at a power of 100 W for 10 minutes.

50 g of a Carbopol ® 940 gel prepared according to the instructions in Example 2 are finally added.

EXAMPLE 7 ACCORDING TO THE INVENTION

The procedure of Comparative Example 3 is followed in order to incorporate kojic acid into liposomes.

2 g of hydroquinone in an aqueous solution buffered to pH 7.5, containing an antioxidant, such as ascorbic acid at a concentration of 0.05%, are then added to the resulting liposomal composition so as to give a total volume of 200 ml.

If desired, the suspension is then converted to a gel in the manner described in Example 1.

EXAMPLE 8 ACCORDING TO THE INVENTION

The procedure of Example 7 is followed except that the hydroquinone and kojic acid are reversed, the amounts of active principle remaining unchanged.

EXAMPLE 9

Use of the Compositions According to Examples 1 to 5 for the Preparation of a Pharmaceutical or Cosmetic Composition The activity of the composition of Example 1, according to the invention, used as a pharmaceutical composition, especially a dermatological composition, or a cosmetic composition, relative to the compositions of Comparative Examples 2 to 5, is examined by carrying out the following experiments in vivo.

Demonstration of the Skin-Lightening Activity

As a first alternative, the skin-lightening activity of the compositions according to the invention is studied using hairless mice with pigmented tails, which are obtained in a proportion of 90% in the litter resulting from two successive crossbreedings, the first of which is carried out by crossbreeding a black female C57 mouse with a male BL6-HRO or eb-HRO mouse, available from the centre de sélection et d'élevage d'animaux de laboratoire (center for the selection and breeding of laboratory animals), abbreviated to CSEAL, of the CNRS in Orléans, and the males of the litter are then cross-bred again with a black female C57 mouse.

A second alternative is to use hairless mice with pigmented ears and black eyes, Skh: HR-2, available from the Temple University of Health Sciences, Central Animal Facility, in Philadelphia.

To perform the experiments, the product in the form of a gel obtained in Examples 1 to 5 is applied for 5 days a week for 6 weeks.

Fragments of epidermis are then removed from the tail or ears, by biopsy, in the zones where the product has been applied and these fragments are placed in NaBr for 2 hours.

Samples of epidermis are placed between two quartz slides. They are dried and then weighed.

This dried and weighed epidermis fragment is then subjected to digestion by trypsin at 37° C. for 48 hours.

This is followed by filtration and centrifugation at 3000 rpm for 30 minutes.

The melaniferous residue is recovered and suspended in distilled water.

The optical density is measured in the conventional manner at 400 nm.

The values recorded are then adjusted to correspond to a weight of 100 mg of epidermis removed. Let:

O.D.T. be the mean value obtained for an untreated control group,

O.D.K. be the mean value obtained for a group treated with the "Kligman trio" taken as a positive reference, O.D.A. be the mean value obtained for the group treated either with the active product according to the invention (I1) or with the comparison active product (A1, A2, A3, A4 or A5, A5 representing the = "Kligman trio").

The percentage activity relative to the Kligman trio is calculated as follows:

$$\text{activity} = \frac{O.D.T. - O.D.A.}{O.D.T. - O.D.K.} \times 100$$

The values obtained with each of the compositions of Examples 1 to 5 are entered in Table I below. It is found that:

even in the form of liposomes, 1% of kojic acid has virtually no activity (A2),

2% of hydroquinone also has virtually no activity in the form of a conventional gel (A4), the combination of 2% of hydroquinone and 1% of kojic acid in a conventional gel has a rather insignificant activity (A1), the combination (I1) of 2% of hydroquinone and 1% of kojic acid in liposomes has a substantial activity which is unexpected and hence very interesting since it reaches almost a third of that of the Kligman trio.

Furthermore, the compositions according to the invention have no side effects and, in particular, do not have the irritant effect of vitamin A acid, which has always placed a significant restriction on the use of the Kligman trio based on the combination of 0.05% of vitamin A acid + dexamethasone as an antiinflammatory steroid + 5% of hydroquinone (comparative composition A5).

Various Examples of dermatological and dermatocosmetic compositions are given below.

EXAMPLE 10 ACCORDING TO THE INVENTION

Cosmetic Preparation in Liposomal Form for Lightening Pigmentation Blemishes

| | |
|---|---|
| hydroquinone | 2 |
| kolic acid | 1 |
| lecithin | 1.8 |
| sitosterol | 0.2 |
| sodium bisulfite | 0.5 |
| gel containing 2.5% of stabilized Carbopol ® 940 | 30 |
| water q.s. | 100 |

The procedure of Example 6, 7 or 8 is followed, the sitosterol being dissolved with the lecithin in methylene chloride, before atomization.

The resulting suspension of liposomes must be protected from light and heat.

TABLE 1

| | Results of skin-lightening activity tests | | | | | |
|---|---|---|---|---|---|---|
| Composition | I1 Liposomes H.Q. + K.A. | A1 H.Q. + K.A. | A2 Liposomes K.A. | A3 Liposomes H.Q. | A4 H.Q. | A5 Kligman trio |
| % activity relative to the Kligman trio | 29 | 13 | 4 | 15 | 3 | 100 |

H.Q. = Hydroquinone
K.A. = Kojic Acid

What is claimed is:

1. A cosmetic or pharmaceutical composition comprising liposomes containing hydroquinone and a kojic acid component selected from the group consisting of kojic acid, a kojic acid salt and a kojic acid ester, the hydroquinone being incorporated in the composition in an amount of from 0.5 to 6% by weight thereof and the kojic acid component being incorporated in the composition in an amount of from 0.5 to 4% by weight thereof.

2. The composition of claim 1, wherein the kojic acid component is incorporated in an amount of from 0.5 to 2% by weight of the composition.

3. The composition of claim 1, wherein the hydroquinone is incorporated in an amount of from 0.5 to 4% by weight of the composition.

4. The composition of claim 1, wherein the kojic acid component is incorporated in an amount of from 0.5 to 2% by weight of the composition and the hydroquinone component is incorporated in an amount of from 0.5 to 4% by weight of the composition.

5. The composition of claim 1, wherein the kojic acid component is incorporated in an amount of about 1% of the composition, and the hydroquinone is incorporated in an amount of about 2% by weight of the composition.

6. A method for lightening the skin, comprising applying to the skin a composition comprising liposomes containing hydroquinone and a kojic acid component selected from the group consisting of kojic acid, a kojic acid salt and a kojic acid ester, wherein the hydroquinone is present in an amount of from 0.5 to 6% by weight of the composition and the kojic acid component is present in an amount of from 0.5 to 4% by weight of the composition.

7. The method of claim 6, wherein the hydroquinone is present in an amount of from 0.5 to 4% by weight of the composition.

8. The method of claim 6, wherein the kojic acid component is present in an amount of from 0.5 to 2% by weight of the composition.

9. The method of claim 6, wherein the hydroquinone is present in an amount of from 0.5 to 4% by weight of the composition and the kojic acid component is present in amount of from 0.5 to 2% by weight of the composition.

* * * * *

UNITED STATES PATENT AND TRADEMARK OFFICE
CERTIFICATE OF CORRECTION

PATENT NO. : 5,279,834
DATED : January 18, 1994
INVENTOR(S): Alain Meybeck It is certified that error appears in the above-identified patent and that said Letters Patent is hereby corrected as shown below:

Title page, column 1:  In Item [22] delete "Jul. 17, 1992" and insert --PCT Filed: Jun. 10, 1988--.

On the title page, item [63] after abandoned insert on line three
--filed as PCT/FR88/00295--.

Signed and Sealed this

Eighteenth Day of June, 1996

*Attest:*

BRUCE LEHMAN

*Attesting Officer*        *Commissioner of Patents and Trademarks*